(12) United States Patent
Kilbane, II et al.

(10) Patent No.: US 6,541,240 B1
(45) Date of Patent: *Apr. 1, 2003

(54) BACTERIAL CLEAVAGE OF ONLY ORGANIC C-N BONDS OF CARBONACEOUS MATERIALS TO REDUCE NITROGEN CONTENT

(75) Inventors: John J. Kilbane, II, Woodstock, IL (US); Claudia Maria Soares Ribeiro, Rio de Janeiro (BR); Mônica Moreira Linhares, Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,613

(22) Filed: Nov. 30, 1999

(51) Int. Cl.$^7$ ............... B09B 3/00; C02F 3/00; C02F 3/02; C12N 1/00; C12N 1/20
(52) U.S. Cl. ............ 435/253.3; 210/600; 210/610; 435/252.1; 435/262.5; 435/822; 435/832; 435/874
(58) Field of Search ............... 210/600, 610; 435/262.5, 822, 253.3, 252.1, 832, 874

(56) References Cited

U.S. PATENT DOCUMENTS

| | | | |
|---|---|---|---|
| 5,002,888 A | | 3/1991 | Kilbane, II et al. ...... 435/252.31 |
| 5,297,625 A | | 3/1994 | Premuzic et al. ........... 166/246 |
| 6,204,048 B1 | * | 3/2001 | Kilbane et al. .......... 435/253.3 |
| 6,221,651 B1 | * | 4/2001 | Kilbane et al. .......... 435/253.3 |

OTHER PUBLICATIONS

Shukla, Onkar P., "Microbial Transformation of Quinline by a Pseudomonas sp.", Applied and Environmental Microbiology, vol. 51, Jun. 1986, pp. 1332–1342.

Schwarz, G. et al, "Microbial Metabolism of Quinoline and Related Compounds. I. Isolation and Characterization of Quinoline–Degrading Bacteria", System Appl. Microbiol. 10, 185–190 (1998).

Grant, D.J.W. et al, "Degradation fo quinoline by a soil bacterium", Microbios 1976, 15, pp. 177–189.

O'Loughlin, E.J. et al, "Isolation, Characterization and Substrate Utilization of a Quinline–Degrading Bacterium", International Biodeterioration and Biodegradation (1996), pp. 107–118.

Asilabie et al, (1990), "microbial Degradation of Quinoline and Methylquinoline", Appl. Environ. Microbiol. 56: 345–351.

* cited by examiner

Primary Examiner—David M. Naff
Assistant Examiner—Deborah K. Ware
(74) Attorney, Agent, or Firm—Sughrue Mion, PLLC

(57) ABSTRACT

A microbial process is provided for selective cleavage of only organic C—N bonds while leaving C—C bonds intact which may be used for reducing the nitrogen content of nitrogen-containing organic carbonaceous materials. Microorganisms of *Pseudomonas ayucida* have been found which have the ability of selective cleavage of organic C—N bonds. A particularly preferred microorganism is *Pseudomonas ayucida* strain ATCC No PTA-806. Other microorganisms useful in the cleavage of organic C—N bonds are Aneurinibacillus sp, *Pseudomonas stutzeri*, Yokenella sp. and *Pseudomonas nitroreducens*.

22 Claims, 3 Drawing Sheets

US 6,541,240 B1

BACTERIAL CLEAVAGE OF ONLY ORGANIC C-N BONDS OF CARBONACEOUS MATERIALS TO REDUCE NITROGEN CONTENT

FIELD OF THE INVENTION

The present invention relates to a process for microbial cleavage of organic C—N bonds and biodenitrogenation of nitrogen-containing organic carbonaceous material thereby. More specifically, total nitrogen from a hydrocarbon-containing medium may be reduced, as well nitrogen may be removed from the hydrocarbon molecule or from a fossil fuel. Microorganisms which have the ability of selective cleavage of organic C—N bonds, particularly microorganisms such as *Pseudomonas ayucida* strain No PTA-806 can be used in the process that is the subject of this invention. The process of the invention is particularly useful in removal of organic nitrogen from fossil fuels, such as nitrogen-containing coal, petroleum oil, lignite and derived synthetic fuels while retaining the calorific value of the fuel.

BACKGROUND INFORMATION

The quality of petroleum is progressively deteriorating as the highest quality petroleum deposits are preferentially produced. Consequently, the concern about the concentration of compounds/contaminants such as sulfur, nitrogen, and metals in petroleum will intensify. These contaminants are not only contributors to environmental pollution resulting from the combustion of petroleum, but also interfere with the processing of petroleum by poisoning catalysts and contributing to corrosion. The selective removal of contaminants from petroleum while retaining the fuel value is a difficult technical challenge.

The selective removal of sulfur from dibenzothiophene with the aid of a bacterium useful for cleaving C—S bonds is taught in U.S. Pat. No. 5,002,888.

U.S. Pat. No. 5,297,625 teaches a method for preparing, isolating and utilizing a microorganism which can metabolize crude oils and other high molecular weight hydrocarbons as a source of energy, and emulsify heavy crudes under the extreme conditions existing in oil reservoirs.

Biorefining of petroleum is therefore a technology soon being commercialized and which may be very promising.

The removal of nitrogen and metals from petroleum is a further potential use of biocatalysts, but so far this area of research has received very little attention.

Quinoline is perhaps the most widely studied organonitrogen compound as regards biodegradation, and quinoline is considered to be representative of many organonitrogen compounds typically found in petroleum. Many aerobic and anaerobic microbial cultures have been found that can degrade quinoline. The majority, if not the entirety, of microbial cultures described in the literature that metabolize quinoline do so by fully degrading it, and can therefore utilize quinoline as a sole source of carbon, energy, and nitrogen.

Shukla, Onkar P., in "Microbial Transformation of Quinoline by a Pseudomonas sp.", Applied and Environmental Microbiology, vol 51, June 1986, p. 1332–1342, reports that a Pseudomonas sp isolated from sewage by enrichment culture on quinoline metabolized this substrate by a novel pathway involving 8-hydroxycoumarin. Such microorganism utilizes quinoline as the sole source of carbon, nitrogen, and energy.

Schwarz, G. et al, in "Microbial Metabolism of Quinoline and Related Compounds. I. Isolation and Characterization of Quinoline-Degrading Bacteria", System. Appl. Microbiol. 10, 185–190 (1988) report that from soil, water and activated sludge 16 bacterial strains were isolated which are able to use quinoline as sole source of carbon and nitrogen. Of the 16 bacterial strains investigated, 13 could be allocated to the genus Pseudomonas. These bacteria are Gram-negative, straight to slightly curved, motile rods, which on HNB-agar form yellowish to cream-colored, circular, smooth or partially rough colonies. The species identified are *Pseudomonas putida* Biovars A and B, *Pseudomonas fluorescens* and *Pseudomonas testosteroni*. It is reported that growth on 2-hydroxyquinoline is common to all strains, which were investigated. With several Pseudomonas species the degradation of quinoline has been studied and 2-hydroxyquinoline was found to be the first intermediate in the degradation pathway.

Grant, D. J. W. et al. In "Degradation of quinoline by a soil bacterium", Microbios 1976, 15, p. 177–189, report that from garden soil a bacterium was isolated which grew aerobically in mineral salts medium with quinoline as sole C source and $NH_4^+$ as N source. During growth with quinoline, 2-hydroxyquinoline accumulated in the culture fluid and later disappeared. 2,6-Dihydroxyquinoline is probably the next intermediate in quinoline biodegradation by aerobic organisms examined in this report since whole cells oxidize it rapidly and completely. Aromatic ring cleavage under aerobic conditions almost invariably follows the formation of a compound with two hydroxyl groups attached to a ring in positions o- or p- to each other.

O'Loughlin, E. J. et al. In "Isolation, Characterization and Substrate Utilization of a Quinoline-Degrading Bacterium", International Biodeterioration and Biodegradation (1996), 107–118 report a Gram (+) rod-shaped organism identified as a Rhodococcus sp. capable of growth utilizing quinoline as the dominant carbon, energy, and nitrogen source. The isolate, designated as Rhodococcus sp. Q1 was also capable of growth on 2-hydroxyquinoline, pyridine, 2,3-dimethyl pyridine, catechol, benzoate, and protocatechuic acid, suggesting a diverse capacity for aromatic ring degradation. Although ring nitrogen was released into the growth medium as ammonium, quinoline degradation was not limited by the availability of inorganic N. A degradation product identified as 2-hydroxyquinoline was identified on the basis of several spectroscopic analyses.

Thus, although the cited literature mentions microbial cultures able to metabolize quinoline by fully degrading it, the use of such cultures in a petroleum biorefining application would require that nitrogen be selectively removed from quinoline leaving the carbon and the calorific value of the molecule intact.

As related in the literature, the metabolic pathways utilized by various aerobic quinoline-degrading microorganisms were shown to initiate the degradation of quinoline by selectively oxidizing and removing nitrogen from quinoline.

While the biodegradation of quinoline has been reasonably well studied there is very little information concerning the use of quinoline-degrading microorganisms to remove nitrogen from petroleum. On the other hand, several quinoline-degrading Pseudomonas were found to have no ability to remove significant levels of nitrogen from crude oil or asphaltene fractions of petroleum (Aislabie et al. 1990, "Microbial Degradation of Quinoline and Methylquinoline", Appl. Environ. Microbiol. 56:345–351).

Therefore there is the need to isolate aerobic microbial cultures capable of utilizing quinoline as a nitrogen source, but incapable of utilizing quinoline as a carbon source, the ability of such cultures to selectively remove nitrogen from petroleum, as well as a process for microbial cleavage selectively of organic C—N bonds and reduction of nitrogen from nitrogen-containing organic carbonaceous material thereby, such goal being achieved by the present invention.

SUMMARY OF THE INVENTION

It is an object of the present invention to provide a microbial process for selective removal of organically bound nitrogen from nitrogen-containing organic carbonaceous materials.

It is another object of the present invention to provide a microbial process for selective nitrogen removal from organic nitrogen-containing fossil and fossil derived fuels.

It is yet another object of the present invention to provide a microorganism and process capable of specific cleavage or formation of C—N bonds in reactions of organic carbonaceous materials, such as in organic synthesis.

It is still another object of the present invention to provide a microorganism and process for specific nitrogen removal from quinoline resulting in the primary organic product of 8-hydroxycoumarin.

It is still another object of the present invention to provide a process using a microorganism which is stable and retains its ability to selectively cleave C—N bonds under conditions suitable for an industrial process for cleavage of organic C—N bonding.

The above and other subjects and advantages, as will become apparent upon reading this description, can be achieved by contacting a nitrogen-containing organic carbonaceous material with a microorganism which has the ability of selective cleavage of organic C—N bonds and production of 8-hydroxycoumarin when grown in a growth medium comprising mineral nutrients and an assimilable source of carbon in the presence of oxygen and the substantial absence of a nitrogen-containing compound except the nitrogen-containing organic carbonaceous material. *Pseudomonas ayucida* strain No PTA-806 having the above properties is particularly preferred.

The above and other objects and advantages, as will become apparent upon reading this description, have been achieved by the pure culture of a microorganism which has been isolated and subjected to processes as set forth in further detail and identified as *Pseudomonas ayucida*. The culture has been deposited under the Budapest Treaty with American Type Culture Collection, 10801 University Blvd, Manassas, Va. 20210-2209, USA, and assigned No PTA-806.

*Pseudomonas ayucida* No PTA-806 may be prepared by inoculating environmental samples derived from sites having present materials of C—N bonding desired to be cleaved, a growth medium comprising mineral nutrients, an assimilable source of carbon, and in substantial absence of a nitrogen-containing compound, except compounds having nitrogen present only in C—N bonding of the type desired to be cleaved; growing the bacterial culture in the presence of oxygen at temperatures about 25° C. to about 35° C. and in the substantial absence of a nitrogen-containing compound except compounds having nitrogen present only in C—N bonding of the type desired to be cleaved for sufficient time to selectively produce *Pseudomonas ayucida* No PTA-806 which has the property of nitrogen metabolism by selective cleavage of C—N bonds in organic carbonaceous materials.

Nitrogen content of nitrogen-containing organic carbonaceous material may be reduced by contacting such nitrogen-containing organic carbonaceous material with the microorganism *Pseudomonas ayucida* strain No PTA-806. The process is especially suitable for use where the nitrogen-containing material is a coal, shale oil or hydrocarbon oil.

Continuous growth of *Pseudomonas ayucida* strain No PTA-806 in the presence of nitrogen-containing shale oil results in the removal of more than 50 wt percent, and preferably more than 68 wt percent, of the organically bound nitrogen as quinoline.

The process for reducing the nitrogen content of the nitrogen-containing organic carbonaceous material occurs by cleavage of organic C—N bonds by the microorganism *Pseudomonas ayucida* strain No PTA-806. The organic nitrogen selective microorganism *Pseudomonas ayucida* No PTA-806 has the ability to selectively reduce the nitrogen content of nitrogen-containing organic carbonaceous material by cleavage of organic C—N bonds by production of 8-hydroxycoumarin when grown in a growth medium comprising mineral nutrients and an assimilable source of carbon in the substantial absence of a nitrogen-containing compound except the nitrogen-containing organic carbonaceous material, and in the presence of oxygen at temperatures about 25° C. to about 35° C. Derivative microorganisms of *Pseudomonas ayucida* No PTA-806 that retain the ability to selectively cleave C—N bonds can also be used in the same fashion for the reduction of the nitrogen content of carbonaceous material.

The above and other objects and advantages have also been achieved by the microorganism which has been isolated and subjected to processes as set forth in further detail and identified as *Pseudomonas ayucida*. The culture has been deposited under the Budapest Treaty with American Type Culture Collection, 10801 University Blvd, Manassas, Va. 20110-2209, USA, and assigned No PTA-806. This microorganism, its production and use for selective cleavage of organic C—N bonds is more fully described in a copending, commonly owned US patent application, which is incorporated herein by reference in its entirety.

DETAILED DESCRIPTION OF THE PREFERRED EMBODIMENTS

Figure 1:
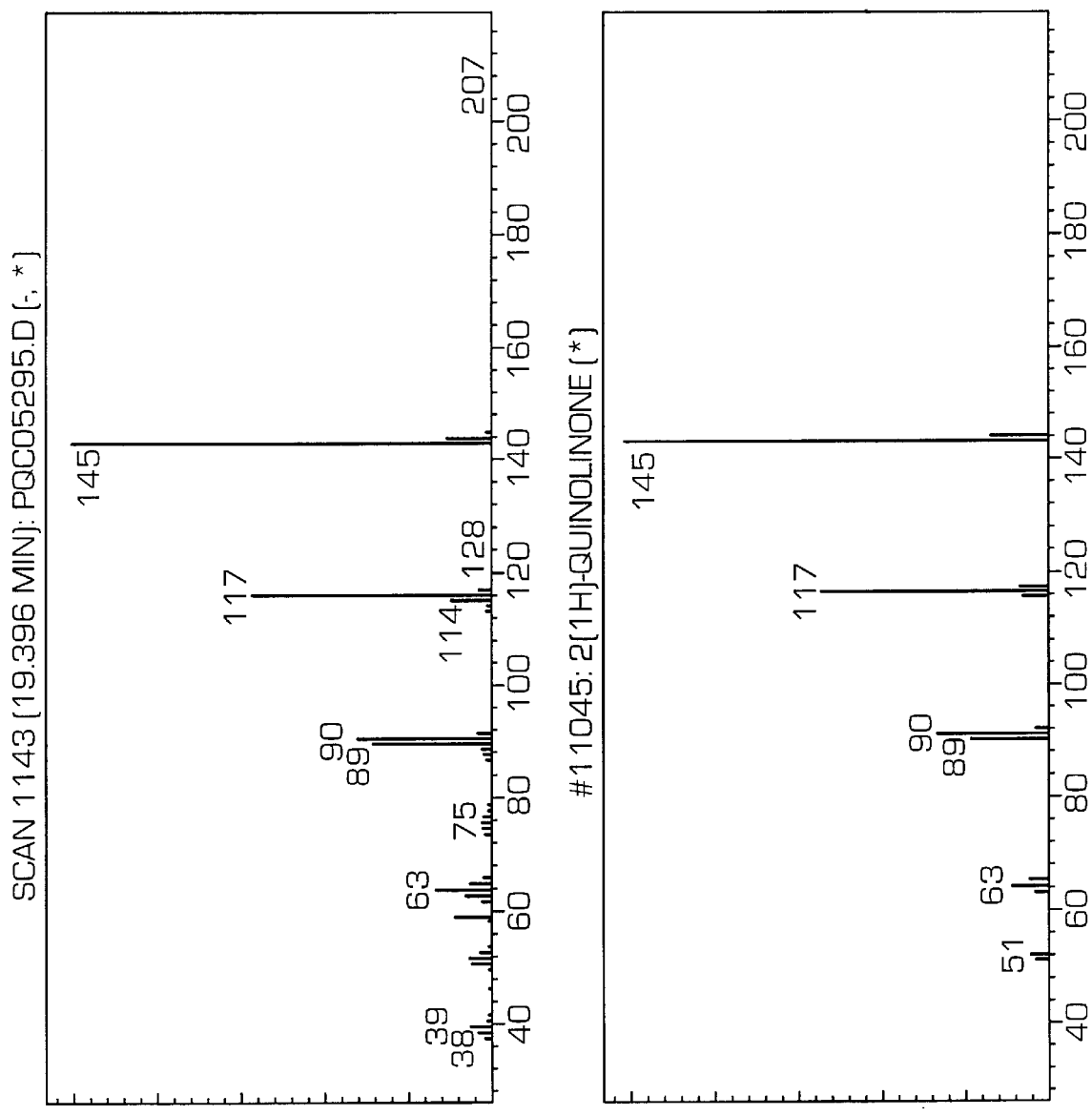
FIG. 1 is a graph which illustrates a comparison of MS data of a metabolite of quinoline produced by *Pseudomonas ayucida* No PTA-806 with 2-quinolinone.

Environmental cultures having a known history of exposure to organonitrogen compounds as well as enrichment cultures using as carbon sources acetate, benzene, benzoic acid, ethanol, glucose, glycerol, nutrient broth, succinate, and toluene and as organic nitrogen compounds quinoline, carbazole and pyridine produce bacterial cultures capable of metabolizing each of the organic nitrogen compounds used. All of the environmental isolates and enrichment cultures tested are found to metabolize organonitrogen compounds by initiating biodegradation of the carbon-carbon bond and/or by utilizing the organonitrogen compound as a carbon and energy source.

A highly successful microorganism for nitrogen utilization from organonitrogen compounds are Pseudomonas strains isolated from enrichment cultures employing quinoline as the sole source of nitrogen. These Pseudomonas species while capable of utilizing organically bound nitrogen fail to show specificity for the oxidation of carbon-nitrogen bonds. This shows the failure of enrichment culture development of a naturally occurring microorganism showing specificity for oxidation of organic C—N bonds. Thus, an unnatural, selective mutation process must be utilized to develop a microorganism having such selective nitrogen metabolism.

Microorganisms having nitrogen-specific metabolic abilities with respect to organic substrates may be developed by selection through chemostat inoculation and shake flask enrichment culture experiments in which nutrients and organically bound nitrogen not normally found in living tissue may be supplied in the substantial absence of other available nitrogen such as ammonia.

The growth media should supply organic and inorganic nutrients for good microorganism growth, but be devoid of inorganic and organic nitrogen-containing compounds desired to be metabolized by the mutant microorganism. A suitable media for growth of microorganisms under organonitrogen conditions may suitably be a composition or mineral nutrients, such as 0.37 g $KH_2PO_4$, 0.25 g $MgSO_4.7H_2O$, 0.07 g $CaCl_2.2H_2O$, 0.02 g $FeCl_3$ and 20.0 g of glucose/glycerol/succinate per liter of distilled, deionized water. Any assimilable carbon source devoid of nitrogen may be used in amounts to support desired microbial growth. Suitable assimilable carbon sources include glucose, glycerol, sodium acetate, sodium benzoate, sodium succinate, and sucrose at concentrations of about 20 mM.

The preferred organonitrogen compound having organic C—N bonds is quinoline. Other suitable compounds having organic C—N bonds are listed hereinbelow.

Environmental samples of soil and/or water may be obtained from petroleum and coal processing sites, compost and other sites where contamination with petroleum hydrocarbons exists.

The environmental samples are used to inoculate chemostat and shake flask enrichment culture experiments to obtain cultures capable of using quinoline as a sole source of nitrogen. In the present invention, all experiments employed the above-defined mineral salt media:

0.37 g $KH_2PO_4$
0.25 g $MgSO_4.7H_2O$
0.07 g $CaCl_2.2H_2O$
0.02 g $FeCl_3$
and 20.0 g of glucose/glycerol/succinate per liter of distilled, deionized water.

This media is adjusted to a pH of 6.5 to 7.0 and nitrogen is supplied in the form of quinoline which is present at concentrations ranging from 1 to 20 mM, or for control experiments $(NH_4)_2SO_4$ is used at a concentration of 1.3 g per liter.

Chemostats and shake flasks are operated at room temperature (25° C.) or 30° C. The working volume of chemostats is one liter and shake flask experiments generally utilize 50 or 100 ml of liquid media. Flow rates of the chemostats are adjusted to achieve hydraulic retention times ranging from two days to as long as a month and the flow rates as well as the organonitrogen test compound are altered as needed to ensure that the chemostats create an environment suitable for the selection of cultures with improved abilities to selectively cleave C—N bonds. This means that the bacterial cell density in the chemostats/shake flasks ranges from $10^2$ to $10^8$ cells/ml, with average cell densities of $10^4$ to $10^5$ cells/ml being maintained. The bacteria isolated from the effluent of chemostats and/or from shake flasks are subjected to chemical mutagenenesis and/or physical mutagenesis using nitrosoguanidine (NTG) and short wave ultraviolet (UV) irradiation respectively. Cell populations are mutagenized under conditions, which result in the death of about 99% of the population. The mutagenized cells are then used to reinoculate chemostats, start additional shake flask experiments, and to streak onto agar plates containing organonitrogen test compounds. Care should be taken to insure that the amount of biomass that is added back to chemostats in the form of inocula is insufficient to provide a significant amount of nitrogen in the form of dead biomass Cells from the effluents of chemostats, shake flasks, and agar plates are routinely tested using the Nitrogen Bioavailability Test Assay described below.

The determination of 16S-rRNA gene sequences for the determination of the species of bacterial isolates was performed by MIDI Labs (Newark, Del.).

Nitrogen Bioavailability Assay

The ability of bacteria to utilize organic nitrogen compounds for growth can be measured by the Nitrogen Bioavailability Assay (NBA). This assay is based on the fact that all life requires some nitrogen for growth and, therefore, a situation can be created whereby quantifying bacterial growth provides a measure of the utilization of any organic or inorganic compound as a source of nitrogen.

Thus, the Nitrogen Availability Assay utilizes defined mineral salts medium in growth tests in which organonitrogen model compounds such as quinoline, pyridine, carbazole, and porphyrin serve as sources of carbon and/or nitrogen. Growth tests are performed using six conditions:

1. Test compound as sole source of carbon and nitrogen;
2. Test compound as sole source of carbon (alternative nitrogen source, ammonia, is available);
3. Test compound as sole source of nitrogen (alternative carbon source, glucose/glycerol/succinate, is available);
4. Test compound present as well as alternative sources of carbon and nitrogen;
5. Only alternative nitrogen (ammonia) and carbon (glucose/glycerol/succinate) sources are available. The test compound is not present.
6. No nitrogen compounds of any kind are present, but alternative carbon (glucose/glycerol/succinate) sources are available.

These six growth conditions constitute a bioassay for the ability of a culture to metabolize organonitrogen compounds. When carbon and nitrogen sources other than the test compounds are needed, they are supplied in the form of a glucose/glycerol/succinate mixture (20 g/L) and as ammonia (20 mM) respectively.

The NBA test may be performed with any organonitrogen test compound which is ordinarily used at a concentration of from 3 mM to 20 mM.

In order to determine the range of organonitrogen compounds that could serve as sole sources of nitrogen for growth for the various pure cultures of the invention various organonitrogen compounds and control compounds are tested according to the Nitrogen Bioavailability Assay procedure. All compounds are highly pure, analytical grade compounds.

These compounds included:
2-Methyl-beta-Naphthothiazole;
2-Methyl Benzothiazole;
2(Methylmercapto)Benzimidazole;
1,1-Methylene Bis (3-Methyl Pipridine);
Thiazole;
1-Butylpyrrolidine;
2-Methylene-1,3,3-Trimethyl Indoline;
2-Methyl-3-Propylpyrazine;
2-Phenylbenzothiazole;
2-Methyl Quinoxaline;
2-Methyl Indoline;
Carbazole;
Quinoline;
Quinazoline;
Quinoxoline;
2,4-Quinolindiol;
Isoquinoline;
3-Methyl Isoquinoline;
Isocarbostyril;
Protoporphyrin;
Pyridine;
Phenyl Benzothiazole;
Nicotinic Acid;
Imidazole;
Indole;
HEPES Buffer;
Urea;
Guanine;
Lysine;
Tryptophan;
Ammonium Chloride.

The various cultures are inoculated into test tubes or shake flasks containing media components appropriate for the six test conditions.

The cultures are then incubated aerobically for 2 to 4 days, at room temperature or at 30° C.

The growth of the cultures is monitored by measuring the turbidity/optical density of the cultures in the various test conditions, or by determining colony forming units.

Test condition no 6 (nitrogen-free sample) is a negative control.

Test conditions no 4 and 5 are positive controls since the samples are amended with both a carbon and nitrogen source and therefore should produce healthy microbial growth unless the test compound is toxic to the culture being tested. In this event only condition no 5 should result in healthy growth.

The amount of bacterial growth observed in test conditions 1, 2 and 3 as compared with the amount of growth observed in test conditions 4, 5 and 6 indicate the ability of cultures to use the organonitrogen test compound as a source of carbon and/or nitrogen.

Cultures which show better growth in test condition no 3 than in test conditions 1 and 2 may be preferentially utilizing the organonitrogen compound as a nitrogen source only.

Spectrophotometric Scans

US/Vis spectrophotometric scans are performed at 240 to 900 nm on a Beckmann DU-65 spectrophotometer. Supernatants from cultures grown using ammonia or quinoline as sole nitrogen sources are compared to identify new peaks formed due to accumulation of metabolites specific to the metabolism of quinoline.

Identification of Metabolites

In order to identify metabolites, Thin Layer Chromatography (TLC) is performed on Silica C-18 plates by the method described by G. K. Watson and R. B. Cain in "Microbial metabolism of the Pyridine Ring", Biochem. J. 146:146–172. Running phase solvents are for example hexane, acetic acid and xylene in the ratio of 5:1:2. Supernatants from bacterial cultures grown with quinoline as the sole source of nitrogen are extracted with ethyl acetate and run on TLC plates.

Alternatively, resting cells may be used, employing washed cell pellets derived from log phase cultures grown with either quinoline or ammonia as nitrogen sources. Concentrated cell suspensions are incubated with 20 mM quinoline for periods ranging from 15 minutes to 16 hours.

Extraction of the supernatants from resting cells as well as growing cells may be carried out either by ethyl acetate solvent extraction or with C18 solid phase extraction cartridges and the extracts analyzed by TLC.

Derivitization of Metabolites

Derivitization of metabolites may be effected by adding semicarbazide-HCl and 2,4 dinitrophenyl hydrazine (2,4-DNPH) to some experiments followed by subsequent extraction and TLC analysis. A typical incubation mixture which utilizes metabolite derivitization consists of 200 mls of Media A (with carbon source) which contains 2 g of cells dry weight, 2 mM semicarbazide-HCl, and 3 mM to 20 mM quinoline as the nitrogen source. The mixture is incubated for 2 hours and the cells are centrifuged. To the supernatant 2,4 DNPH is added, the mixture is left overnight and extracted with ethyl acetate, then separated on a TLC plate and the spots identified.

Gas Chromatography/Mass Spectrometry

GC/MS analysis is performed on extracts derived from growing and resting cell cultures exposed to quinoline, and on compounds eluted from spots observed on TLC plates.

Extraction of the supernatants from resting cells as well as growing cells may be carried out either by ethyl acetate solvent extraction or with C-18 solid phase extraction cartridges. TLC spots of possible metabolites are analyzed by GC/MS.

Mass spectrographs are compared with various libraries of mass spectrograph data prepared from known standard compounds.

Assessment of the Ability of *Pseudomonas ayucida* No PTA-806 in the Cleavage of Organic C—N Bonds In order to assess the ability of *Pseudomonas ayucida* No PTA-806 of cleaving organic C—N bonds, this microorganism is made to grow in ModA medium using quinoline as the sole nitrogen source. One liter of culture OD600=1.67 is produced, which is harvested and the cell pellet is resuspended in 100 mls of ModA medium. The culture is divided into two 50 ml portions and 3 ml of shale oil (1.7 weight % nitrogen) is added to each. Then, the cultures are incubated under agitation at room temperature overnight (16 hours), the oil is separated and analyzed. The amount of quinoline present in oil samples is determined by GC, the area under the peak being corresponding to a retention time for quinoline.

Preparation of a Pure Culture of *Pseudomonas ayucida* No PTA-806

The preparation of a pure culture of a microorganism capable of organic C—N cleavage while maintaining the calorific value of the organic molecule according to the present invention comprises collecting environmental samples obtained from petroleum-contaminated locations, inoculating chemostats and effecting shake flask enrichment culture experiments in which 3 mM to 20 mM quinoline is supplied as the sole source of nitrogen. After the initial period of toxicity of quinoline, bacterial growth yields mixed and pure cultures which are tested using the Nitrogen Bioavailability Assay to detect cultures capable of using quinoline as a nitrogen source, but not as a carbon source.

Quinoline-utilizing cultures initially obtained from the chemostats are found to fully degrade quinoline, utilizing it as a carbon as well as a nitrogen source. Then, the flow rates of the chemostats are increased so as to decrease the hydraulic retention times from 96 hours to 4 hours. Cells from the chemostat effluent are mutagenized and returned to the chemostat. Eventually a pure culture is obtained that yielded Nitrogen Bioavailability Assay results that indicated that quinoline was used as a nitrogen, but not as a carbon source. A partial sequence of the 16S-rRNA gene of this gram negative, rod-shaped bacteria was determined identifying it as *Pseudomonas ayucida* which was deposited in the under No PTA-806. *P. monteilii*, which shows 99% homology, and *Pseudomonas nitroreducens* and *Pseudomonas pseudoalcaligenes pesudoalcaligenes*, which both show 98.3% homology, are closely related, but not identical to *Pseudomonas ayucida* No PTA-806.

*Pseudomonas ayucida* No PTA-806 has a cell doubling time of 4.25 hours when grown in defined salts medium at 30° C. with quinoline serving as the sole nitrogen source.

Substrate range and specificity tests were also carried out for the microorganism of the invention.

*Pseudomonas ayucida* No PTA-806 is found to grow on urea, tryptophan, lysine, guanine, nicotinic acid, quinoline, 3,4-dihydro-(1H)-quinolinone, 2,4-quinolinediol, 8-hydroxyquinoline, and quinoxaline.

It should be noted that growth with urea, tryptophan, lysine, guanine and nicotinic acid as nitrogen sources is a common ability possessed by a large number of aerobic bacteria and most likely has no relationship to metabolic pathways relevant to the utilization of quinoline.

The culture grew in the presence of all of the test compounds except 1-butylpyrrolidine and 2-methylene-1,3, 3-trimethyl indoline when quinoline was simultaneously present as an alternate nitrogen source.

TLC was performed on the extracts derived from the culture supematants of *Pseudomonas ayucida* No PTA-806 grown with quinoline as sole nitrogen source, as well as pre-grown cells incubated for various times in the presence of quinoline as described hereinbefore. Controls of the culture grown using ammonia rather than quinoline as a nitrogen source were included in all experiments. Additionally, pure chemicals that are possible metabolites of quinoline such as protocatachuate, catechol, pyruvic acid and p-hydroxy benzoic acid, formamide, 8-hydroxyquinoline and succinic acid dimethyl ester were included as controls to determine if these compounds were formed during the microbial degradation of quinoline. Two spots having Retardation factors (Rf) values of 0.73 and 0.88 were identified as possible metabolites of quinoline by *Pseudomonas ayucida* No PTA-806 as these compounds were found only in samples derived from the incubation of *Pseudomonas ayucida* No PTA-806 with quinoline. Cells of the same culture incubated with ammonia did not produce these compounds. TLC alone could not accurately identify these two compounds so the spots were scraped from TLC plates, eluted with ethyl acetate and subjected to GC/MS analysis.

Figure 2:
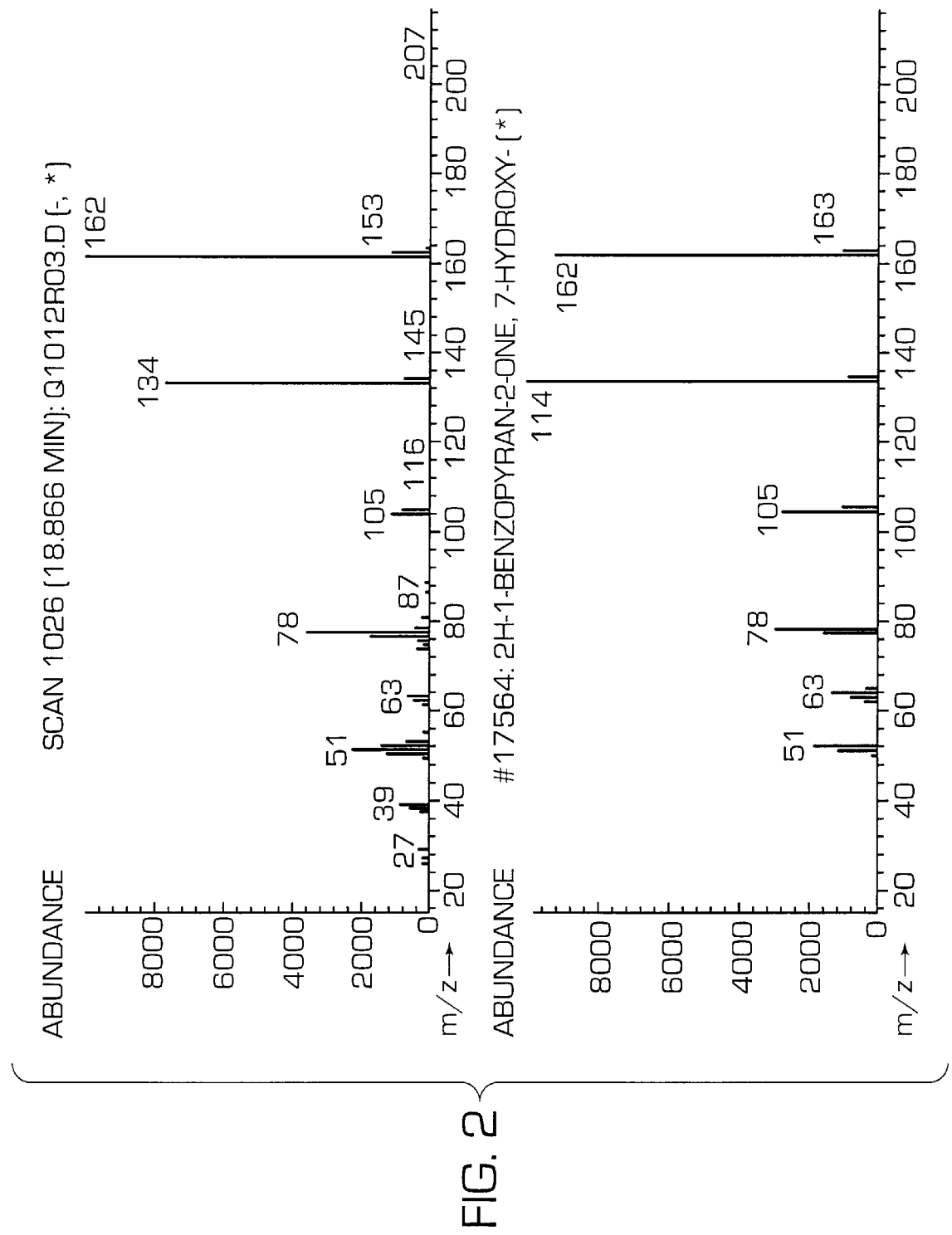
FIG. 2 is a graph which illustrates a comparison of MS data of a metabolite of quinoline produced by *Pseudomonas ayucida* No PTA-806 with 7-hydroxy-2H-1-benzopyran-2-one (7-hydroxycoumarin).

Gas Chromatography/Mass Spectroscopy (GC/MS) analysis may be further performed on extracts derived from growing cell as well as resting cells of *Pseudomonas ayucida* No PTA-806, allowing for the possible detection of metabolites that do not yield detectable spots in TLC. Two compounds may be identified as metabolites of quinoline produced by *Pseudomonas ayucida* No PTA-806: 2-quinolinone and 8-hydroxycoumarin. MS data comparing these metabolites with authentic 2-quinolinone and 7-hydroxy coumarin (7-hydroxy-2H-1-benzopyran-2-one) are shown in FIGS. 1 and 2 respectively.

GC/MS may be used to further analyze the metabolites of quinoline produced by *Pseudomonas ayucida* No PTA-806, the relative abundance of these two metabolites being quantified with resting cells exposed to quinoline for various times. The results are shown in TABLE 1 below.

TABLE 1

| Metabolite | 15 min. | 60 min. | 4 hours |
| --- | --- | --- | --- |
| 2-quinolinone | 47.8% | 37.3% | 17.2% |
| 8-hydroxycoumarin | 8.4% | 17.3% | 16.7% |

Figure 3:
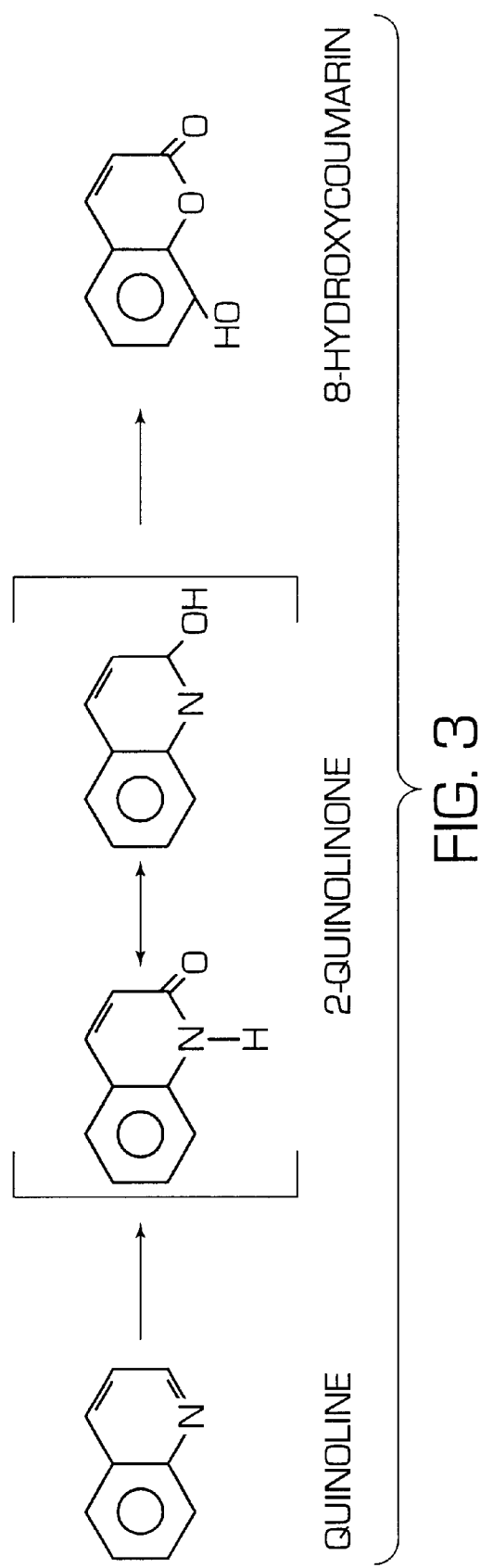
FIG. 3 is a schematic representation of the partial pathway for the degradation of quinoline by *Pseudomonas ayucida* No PTA-806.

The data set forth in Table 1 are expressed as a percentage of the total area of all peaks present in the chromatograph (with the exception of quinoline). These data strongly indicate that quinoline is first converted to 2-quinolinone and then to 8-hdyroxycoumarin, with other intermediate metabolites as well. FIG. 3 attached illustrates the structures of 2-quinolinone and 8-hydroxycoumarin, these two compounds constituting a partial pathway for the biotransformation of quinoline by *Pseudomonas ayucida* No PTA-806

The oxygenation of the carbon atom adjacent to the nitrogen atom in quinoline to form 2-quinolinone is consistent with the selective cleavage of C—N bonds in quinoline by *Pseudomonas ayucida* No PTA-806.

Moreover, the results of the substrate range tests which indicate that *Pseudomonas ayucida* No PTA-806 can utilize quinoline, 3,4-dihydro-2(1H)-quinolinone, 2,4-quinolinediol, 8-hydroxyquinoline and quinoxaline are also consistent with the partial pathway depicted in FIG. 3.

The fact that 8-hdyroxycoumarin contains no nitrogen demonstrates that *Pseudomonas ayucida* No PTA-806 is capable of selective removal of nitrogen from quinoline.

The lack of utilization of quinoline or hydroxy coumarin as carbon sources for the growth of this culture and the lack of further detectable metabolites of quinoline suggests that *Pseudomonas ayucida* No PTA-806 does not further degrade 8-hydroxycoumarin. The decreased abundance of 8-hydroxycoumarin with longer incubation times is believed to be due to 8-hydroxycoumarin becoming increasingly bound to biomass and difficult to recover quantitatively.

Contrary to many quinoline-degrading microorganisms which produce pink, green and brown metabolites, *Pseudomonas ayucida* No PTA-806 produces no colored metabolites.

Other Cultures Having the Ability of Selective Cleavage of Organic C—N Bonding The laboratory procedures of enrichment culture/directed evolution that have been described for the isolation of

*Pseudomonas ayucida* No PTA-806 was also used to isolate several other mesophilic and thermophilic bacterial cultures that can selectively remove nitrogen from organic compounds. Naturally occurring microorganisms were not found to be capable of selectively cleaving carbon-nitrogen bonds. However, by following the enrichment culture/directed evolution procedures described here suitable bacteria possessing the desired C—N bond cleaving trait could be isolated and several examples are cited here.

Derivatives of *Pseudomonas ayucida* No PTA-806

Derivatives of *Pseudomonas ayucida* No PTA-806 have been selected which have improved ability to utilize quinoxoline as a sole nitrogen source. This derivative culture retains its ability to selectively cleave C—N bonds in quinoline and has an increased substrate range for the metabolism of additional organonitrogen compounds such as quinazoline and isoquinoline. Similarly, derivatives of *Pseudomonas ayucida* No PTA-806 that are resistant to antiobiotics, either by the isolation of chromosomal mutations or by the introduction of suitable plasmids, retain the ability to selectively cleave C—N bonds in quinoline and other organonitrogen compounds.

Aneurinibacillus sp.

Equally useful in the present process for the selective cleavage of organic C—N bonding is a thermophilic culture, which grows at 55° C. with pyridine as its sole source of nitrogen. The DNA sequence of its 16S-RNA gene sequence indicates that this culture is an Aneurinibacillus sp. most closely related to *Aneurinibacillus migulanus* and *Aneurinibacillus aneurinolyticus*, and somewhat related to *Bacillus stearothermophilus*. Naturally occurring cultures of Aneurinibacillus are not known to be capable of selectively utilizing pyridine as a sole nitrogen source but the mutant strain of Aneurinibacillus isolated from enrichment culture/directed evolution experiments employing growth medium devoid of inorganic nitrogen is yet another example of the process that can be used to obtain bacteria that possess the desired ability to selectively cleave C—N bonds that can subsequently be used in a process for the removal of nitrogen from carbonaceous material.

Nitrogen Availability Assays show that this microorganism is able to utilize pyridine as a sole nitrogen source, no utilization of pyridine as a carbon source being observed.

The growth curve for this microorganism on pyridine as sole nitrogen source at 55° C. was determined by adding pyridine at the concentration of 3 mM to the Modified A medium in a 300 ml shake flask with a side arm klett tube to take klett/turbidity readings. Inoculums from log phase cultures were used in studying the growth kinetics of the culture. The exponential growth rate for the microorganism was determined as 0.13 hours with a generation time of 7.55 hours. All experiments were in triplicate.

Parameters such as influence of initial pH, temperature and concentration of nitrogen on growth were investigated.

It was found that this culture grows well at a pH between 4 and 10, preferably 6 and 9, incubation lasting from 6 to 7 days.

Temperature conditions for growth with pyridine as sole nitrogen source extend from 30 to 55° C., with no growth being observed beyond 55° C.

The concentration of nitrogen required by Aneurinibacillus sp. for growth was investigated using ammonium chloride and pyridine as sole nitrogen sources in modified medium A, at pH 7 and 55° C. The results of growth experiments with this culture provided with pyridine or ammonium chloride at concentrations ranging from 0.01 mM to 10 mM indicate that a minimum nitrogen concentration of 0.5 mM is needed for growth and maximum growth was observed at nitrogen concentrations of 3 to 5 mM. Pyridine apparently is inhibitory to this culture at concentrations higher than 10 mM.

Substrate range and specificity tests were carried out for this culture. Experiments were performed during 2 to 3 weeks of incubations in sterile tubes with 3 mM concentration of the test compounds and an incubation volume of 5 ml. The culture showed growth on urea, tryptophan, lysine, guanine, pyridine and nicotinic acid. Growth on nicotinic acid was accompanied by a color change (red).

UV/V is scanning in the range from 200 to 900 nm wavelengths was carried out on the supematants of the culture, which were grown with pyridine as sole nitrogen source.

Aneurinibacillus sp pure cultures prepared according to the methods described herein and grown with pyridine as sole source of nitrogen showed complete disappearance of the absorption maximum peak for pyridine which is around 260 nm. No new spectrophotometric peaks that might be due to metabolites of pyridine were detected. The culture was incubated for 4 days prior to scanning. Control samples where ammonium chloride was present as a nitrogen source showed no peaks at all.

TLC was also employed for identifying metabolites of pyridine metabolism by Aneurinibacillus sp pure cultures. Metabolites were detected but their chemical structures have not yet been determined. The growth of this culture using pyridine as a nitrogen but not as a carbon source suggests that the metabolites are the result of the selective cleavage of C—N bonds.

The Aneurinibacillus sp has been designated as Aneurinibacillus sp. IGTN4T and was deposited with the American Type Culture Collection, located at 10801 University Blvd., Manassas, Va. 20110–2209, under the terms of the Budapest Treaty, on Aug. 9, 2002, and assigned accession number PTA-4581.

*Pseudomonas stutzeri*

This culture is prepared by the methods described hereinbefore. This culture is able to utilize carbazole as a sole nitrogen source but dose not utilize carbazole as a source of carbon. Experimental results lead to the conclusion that C—N bonds in carbazole are selectively cleaved by the *Pseudomonas stutzer* culture isolated here although the specific metabolites produced have not yet been determined.

Yokenella sp.

The behavior of this culture is very similar to that of the *Pseudomonas stutzeri* culture. The Yokenella sp. culture is prepared according to the principles described hereinbefore. This culture is able to utilize carbazole as a sole nitrogen source but dose not utilize carbazole as a source of carbon. Experimental results lead to the conclusion that C—N bonds in carbazole are selectively cleaved by the Yokenella sp. culture isolated here although the specific metabolites produced have not yet been determined.

*Pseudomonas nitroreducens*

The behavior of this culture is very similar to that of the *Pseudomonas ayucida* culture. The range of growth temperature is between 27° C. to 33° C. Experimental results show that growth with quinoline as sole source of nitrogen is indicated. When grown in a medium identical to that described for *Pseudomonas ayucida* and containing quinoline in a 3.4 mM concentration as the sole source of nitrogen, *Pseudomonas nitroreducens* reduced the total nitrogen content of the medium up to 85%.

A partial sequence of the 16S-rRNA gene of this gram negative, rod-shaped bacteria was determined identifying it as *Pseudomonas nitroreducens. P. alcaligenes* which shows 98.9% homology and *P. stutzeri* which shows 98.3% homology, are closely related but not identical to *Pseudomonas nitroreducens*.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

Therefore, the researches conducted by the Applicant demonstrate that pure cultures (and derivatives of these cultures) of various mesophilic and thermophilic bacteria can be isolated using the enrichment culture/directed evolution procedure described here that can be useful in a process for the selective removal of nitrogen from organic materials. In particular two unique, patently distinguishing features that have relevance to a denitrogenation process have been demonstrated in the bacterial cultures isolated by the Applicant:

The ability to selectively remove nitrogen from organo-nitrogen compounds such as quinoline, carbazole, and pyridine, The inability to use compounds such as quinoline, carbazole, and pyridine as a carbon source;

The present invention will now be illustrated by a specific example, which should not be construed as limiting the invention.

EXAMPLE

A petroleum biodenitrogenation test according to the principles of the invention demonstrates the ability of *Pseudomonas ayucida* No PTA-806 to remove nitrogen from shale oil. *Pseudomonas ayucida* No PTA-806 was grown as described hereinbefore, using quinoline as a sole nitrogen source. Then duplicate washed concentrated cell suspensions were incubated with shale oil samples for 16 hours at 30° C. The control sample consisted of shale oil added to sterile ModA medium which was incubated for 16 hours at 30° C. After incubation the petroleum samples were recovered and analyzed. The results are listed in TABLE 2 below which indicate that pre-grown *Pseudomonas ayucida* No PTA-806 cells are capable of removing about 5% of the total organic nitrogen and about 68% of quinoline from shale oil during an overnight (16 hour) incubation. Results in Table 2 are reported as a percentage of the neat oil, except for the amount of quinoline which is reported as the area under the peak corresponding to the retention time of quinoline in gas chromatographs.

TABLE 2

| Element | Control Oil | Biotreated Oil n° 1 | Biotreated Oil n° 2 |
| --- | --- | --- | --- |
| Carbon, wt % | 85.01 | 85.21 | 84.87 |
| Hydrogen, wt % | 9.69 | 9.81 | 9.81 |
| Nitrogen, wt % | 1.71 | 1.63 | 1.62 |
| Sulfur, wt % | 1.41 | 1.34 | 1.36 |
| Quinoline (GC peak area) | 177,495 | 58,502 | 57,415 |

Data in Table 2 demonstrate therefore that total nitrogen in petroleum may be reduced in 5% as a result of the exposure of the petroleum oil to the pure culture of the invention. Moreover, about 68% of the quinoline present in petroleum may be removed as a consequence of the biotreatment and therefore biorefining processes for the selective removal of nitrogen from petroleum may be achieved in the presence of biocatalysts such as the *Pseudomonas ayucida* No PTA-806 of the inventive process.

We have found that *Pseudomonas ayucida* No PTA-806, and its derivatives, uniquely metabolizes nitrogen by cleavage of the C—N bonding in organic carbonaceous materials, for example, in the metabolism of quinoline. Such property renders *Pseudomonas ayucida* No PTA-806 a specific agent for use in organic chemical synthesis for cleavage of organic C—N bonding which may be used in various organic process synthesis systems. Likewise, the unique properties of *Pseudomonas ayucida* No PTA-806 and its derivatives may be utilized in denitrogenating degradation of a wide variety of organic materials by cleavage of organic C—N bonding.

Further, cell-free extracts comprising crude cell lysates or purified enzyme solutions may be prepared as a lysate from the microorganisms of the invention by lysis processes. Any process providing a cell-free solution is suitable as long as enzymes responsible for the selective cleavage of C—N bonds are retained in the product. An enzyme or enzymes contained within the above microorganisms may be separated by enzyme extraction processes and are capable of cleavage of C—N bonds in organic carbonaceous materials. The enzyme or enzymes may be used in extracted form or may be further purified and used in purified form. As used herein, the term "enzyme" or "enzymes" is meant to include a single enzyme or a composition of enzymes in an extracted form or purified form. Use of these nitrogen specific reactant agents of an extract comprising crude cell lysates and/or a purified enzyme or enzymes derived from the specified microorganisms permits use of selective organic nitrogen removal processes using aqueous or non-aqueous media and temperatures in excess of those which allow microbial growth.

We claim:

1. A biologically pure culture of a bacterium that selectively cleaves only organic C—N bonds, while leaving C—C bonds intact, obtained by a process comprising the steps of:

a) culturing a bacterial strain in a selection medium comprising a mineral nutrient growth medium, an assimilable source of carbon, a compound having nitrogen present only in C—N bonding of the type desired to be cleaved, and the absence of any other source of nitrogen, b) subjecting the culture to chemical and/or physical mutagenesis, and c) performing an assay to determine whether the bacterium selectively cleaved organic C—N bonds while leaving C—C bonds intact, thereby obtaining a bacterium that selectively cleaves organic C—N bonds, while leaving C—C bonds intact.

2. The bacterium according to claim 1 wherein the compound having nitrogen present only in C—N bonding of the type desired to be cleaved is selected from the group consisting of aromatic and cyclic aliphatic carbonaceous materials having C—N bonds selected from the group consisting of quinoline, hydroxyquinolines, methylquinolines, ethylquinolines, quinoxalines, hydroxyquinoxalines, methylquinoxalines, ethylquinoxalines, and derivatives thereof.

3. The bacterium according to claim 1 wherein the chemical mutagenesis is performed using nitrosoguanidine.

4. The bacterium according to claim 1 wherein the physical mutagenesis is performed using short wave ultraviolet radiation.

5. A process for cleavage of organic C—N bonds through the use of a bacterium, wherein the bacterium is isolated by selection for its ability to selectively cleave only organic C—N bonds while leaving C—C bonds intact, wherein the process comprising the steps of:
   contacting an organic carbonaceous material selected from the group consisting of crude oil, petroleum distillates, hydrocarbon-based liquid, coal, pure organonitrogen chemicals having C—N bonds and mixed organonitrogen chemicals having C—N bonds, with the bacterium,
   incubating said organic carbonaceous material and the bacterium under metabolic conditions required for growth of the bacterium to allow for selective cleavage of only C—N bonds, wherein said conditions include
      a) a growth medium comprising mineral nutrients and an assimilable source of carbon,
      b) the substantial absence of a nitrogen-containing compound except said organic carbonaceous material, and
      c) the presence of oxygen, and
   separating the bacterium from said organic carbonaceous material to recover a product with reduced nitrogen content.

6. A process according to claim 5 wherein said metabolic conditions include maintaining pH at about 5 to about 9.

7. A process according to claim 5 which includes maintaining temperature at about 15 to 110° C.

8. A process according to claim 5 which includes maintaining temperature at about 30 to 55° C.

9. A process for cleavage of organic C—N bonds through the use of a bacterium, wherein the bacterium is isolated by selection for its ability to selectively cleave only organic C—N bonds while leaving C—C bonds intact, comprising the steps of:
   contacting an organic compound selected from the group consisting of aromatic and cyclic aliphatic carbonaceous materials having C—N bonds selected from the group consisting of quinoline, hydroxyquinolines, methylquinolines, ethylquinolines, quinoxalines, hydroxyquinoxalines, methylquinoxalines, ethylquinoxalines, and derivatives thereof, with the bacterium,
   incubating said organic carbonaceous material and the bacterium under metabolic conditions required for growth of the bacterium to allow for selective cleavage of only C—N bonds, wherein said conditions include
      a) a growth medium comprising mineral nutrients and an assimilable source of carbon,
      b) the substantial absence of a nitrogen-containing compound except said organic carbonaceous material, and
      c) the presence of oxygen, and
   separating the bacterium from said organic carbonaceous material to recover a product with reduced nitrogen content.

10. A process according to claim 9 wherein said metabolic conditions include maintaining temperature at about 15 to about 110° C.

11. A process according to claim 9 wherein said metabolic conditions include maintaining temperature at about 30 to about 55° C.

12. A process according to claim 9 wherein said metabolic conditions include maintaining pH at about 5 to about 9.

13. A process for cleavage of organic C—N bonds using a bacterium that selectively cleaves only organic C—N bonds, while leaving C—C bonds intact, comprising the steps of:
   a) providing a bacterium that selectively cleaves only organic C—N bonds, while leaving C—C bonds intact, wherein the bacterium is produced through a selection process comprising the steps of:
      i) culturing a bacterial strain in a selection medium comprising a mineral nutrient growth medium, an assimilable source of carbon, a compound having nitrogen present only in C—N bonding of the type desired to be cleaved, and the absence of any other source of nitrogen,
      ii) subjecting the culture to chemical and/or physical mutagenesis, and
      iii) performing an assay to determine whether the bacterium selectively cleaved organic C—N bonds while leaving C—C bonds intact;
   b) contacting an organic carbonaceous material selected from the group consisting of crude oil, petroleum distillates, hydrocarbon-based liquid, coal, pure organonitrogen chemicals having C—N bonds and mixed organonitrogen chemicals having C—N bonds, with the bacterium;
   c) incubating said organic carbonaceous material and the bacterium in a cleavage medium comprising a mineral nutrient growth medium, an assimilable source of carbon, the substantial absence of a nitrogen-containing compound except said organic carbonaceous material, and the presence of oxygen, to allow for selective cleavage of only C—N bonds; and
   d) separating the bacterium from said organic carbonaceous material to recover a product with reduced nitrogen content.

14. A process according to claim 13 wherein pH of said cleavage medium is maintained at about 5 to about 9.

15. A process according to claim 13 wherein said organic carbonaceous material and the bacterium are incubated at a temperature of from about 15 to 110° C.

16. A process according to claim 13 wherein said organic carbonaceous material and the bacterium are incubated at a temperature of from about 30 to 55° C.

17. A process according to claim 13 wherein the bacterium is selected from the group consisting of *Pseudomonas ayucida* strain ATCC No PTA-806 and a derivative of *Pseudomonas ayucida* strain ATCC No PTA-806.

18. A process for cleavage of organic C—N bonds using a bacterium that selectively cleaves only organic C—N bonds, while leaving C—C bonds intact, comprising the steps of:
   a) providing a bacterium that selectively cleaves only organic C—N bonds, while leaving C—C bonds intact, wherein the bacterium is produced through a selection process comprising the steps of:
      i) culturing a bacterial strain in a selection medium comprising a mineral nutrient growth medium, an assimilable source of carbon, a compound having nitrogen present only in C—N bonding of the type desired to be cleaved, and the absence of any other source of nitrogen,
      ii) subjecting the culture to chemical and/or physical mutagenesis, and iii) performing an assay to determine whether the bacterium selectively cleaved organic C—N bonds while leaving C—C bonds intact;

b) contacting an organic compound selected from the group consisting of aromatic and cyclic aliphatic carbonaceous materials having C—N bonds selected from the group consisting of quinoline, hydroxyquinolines, methylquinolines, ethylquinolines, quinoxalines, hydroxyquinoxalines, methylquinoxalines, ethylquinoxalines, and derivatives thereof, with the bacterium;

c) incubating said organic carbonaceous material and the bacterium in a cleavage medium comprising a mineral nutrient growth medium, an assimilable source of carbon, the substantial absence of a nitrogen-containing compound except said organic carbonaceous material, and the presence of oxygen, to allow for selective cleavage of only C—N bonds; and d) separating the bacterium from said organic carbonaceous material to recover a product with reduced nitrogen content.

19. A process according to claim 18 wherein pH of said cleavage medium is maintained at about 5 to about 9.

20. A process according to claim 18 wherein said organic carbonaceous material and the bacterium are incubated at a temperature of from about 15 to 110° C.

21. A process according to claim 18 wherein said organic carbonaceous material and the bacterium are incubated at a temperature of from about 30 to 55° C.

22. A process according to claim 18 wherein the bacterium is selected from the group consisting of *Pseudomonas ayucida* strain ATCC No PTA-806 and a derivative of *Pseudomonas ayucida* strain ATCC No PTA-806.

* * * * *